(12) United States Patent
Lesch et al.

(10) Patent No.: US 10,086,181 B2
(45) Date of Patent: *Oct. 2, 2018

(54) METHODS AND DEVICES FOR TREATING SINUSITIS

(71) Applicant: ENTELLUS MEDICAL, INC., Plymouth, MN (US)

(72) Inventors: Paul Lesch, Lino Lakes, MN (US); Aaron Piddie, Bloomington, MN (US); Peter T. Keith, Lanesboro, MN (US); Anthony J. Hanson, Chaska, MN (US); John R. Drontle, Buffalo, MN (US)

(73) Assignee: ENTELLUS MEDICAL, INC., Plymouth, MN (US)

( * ) Notice: Subject to any disclaimer, the term of this patent is extended or adjusted under 35 U.S.C. 154(b) by 35 days.

This patent is subject to a terminal disclaimer.

(21) Appl. No.: 15/049,800

(22) Filed: Feb. 22, 2016

(65) Prior Publication Data

US 2016/0166814 A1    Jun. 16, 2016

Related U.S. Application Data

(63) Continuation of application No. 13/674,734, filed on Nov. 12, 2012, now Pat. No. 9,283,360.

(Continued)

(51) Int. Cl.
*A61M 29/00* (2006.01)
*A61M 29/02* (2006.01)
*A61B 17/24* (2006.01)

(52) U.S. Cl.
CPC ............. *A61M 29/02* (2013.01); *A61B 17/24* (2013.01); *A61M 2029/025* (2013.01)

(58) Field of Classification Search
CPC ............... A61B 17/24; A61B 17/3421; A61B 17/12104; A61B 17/12136; A61B 1/233;
(Continued)

(56) References Cited

U.S. PATENT DOCUMENTS 2,525,183 A    10/1950  Robison
3,800,788 A     4/1974  White
(Continued)

FOREIGN PATENT DOCUMENTS

EP    0 129 634 A1    1/1985
EP      159815 A1   11/2005
(Continued)

OTHER PUBLICATIONS

Iro, H., J. Zenk, "A new device for frontal sinus endoscopy: First Clinical Report", Department of Otorhinolaryngology, University of Eralngen-Nuremberg, Germany. Otorhinolaryngology, Head and Neck Surgery vol. 125 No. 6, Dec. 2001, pp. 613-616 (4 pages).
(Continued)

*Primary Examiner* — Elizabeth Houston
*Assistant Examiner* — Mohamed Gabr
(74) *Attorney, Agent, or Firm* — Vista IP Law Group LLP

(57) ABSTRACT

The invention describes a sinus balloon catheter and methods of use. Specifically a sinus balloon catheter for dilating a sinus cavity lumen is provided with a tip that can be extended. The catheter comprises a guide tube with a proximal and distal end, a sleeve member, a balloon disposed upon the sleeve member and a rounded tip arranged at the distal end and extendable along with the extension of the sleeve member.

8 Claims, 6 Drawing Sheets

Related U.S. Application Data

(60) Provisional application No. 61/558,142, filed on Nov. 10, 2011.

(58) Field of Classification Search
CPC ........... A61B 1/01; A61B 1/018; A61B 1/227; A61B 1/267; A61B 1/313; A61B 34/20; A61B 2017/246; A61B 2017/00367; A61M 29/02; A61M 2210/0618; A61M 2210/0681; A61M 2029/025; A61M 25/0054; A61M 25/0662; A61M 2025/1079; A61F 2002/9517; A61F 2/2418; A61F 2/2436; A61F 2/2439
USPC ............................................ 604/96.01, 97.01
See application file for complete search history.

(56) References Cited

U.S. PATENT DOCUMENTS

| | | |
|---|---|---|
| 4,737,141 A | 4/1988 | Spits |
| 5,024,658 A | 6/1991 | Kozlov et al. |
| 5,021,043 A | 7/1991 | Becker et al. |
| 5,169,386 A | 12/1992 | Becker et al. |
| 5,222,951 A * | 6/1993 | Abidin .................. A61B 17/02 30/162 |
| 5,391,199 A | 2/1995 | Ben-Haim |
| 5,415,634 A | 5/1995 | Glynn et al. |
| 5,443,489 A | 8/1995 | Ben-Haim |
| 5,466,222 A | 11/1995 | Ressemann et al. |
| 5,470,315 A | 11/1995 | Adams |
| 5,569,274 A | 10/1996 | Rapacki et al. |
| 5,591,129 A * | 1/1997 | Shoup ................ A61M 25/0075 604/103.1 |
| 5,632,762 A | 5/1997 | Myler |
| 5,645,628 A | 7/1997 | Thome |
| 5,795,325 A | 8/1998 | Valley et al. |
| 5,964,767 A | 10/1999 | Tapia et al. |
| 6,083,188 A | 7/2000 | Becker |
| 6,090,132 A | 7/2000 | Fox |
| 6,113,567 A | 9/2000 | Becker |
| 6,206,870 B1 | 3/2001 | Kanner |
| 6,238,364 B1 | 5/2001 | Becker |
| 6,491,940 B1 | 12/2002 | Levin |
| 6,543,452 B1 | 4/2003 | Lavigne |
| D501,677 S | 2/2005 | Becker |
| 6,851,424 B2 | 2/2005 | Scopton |
| 7,520,876 B2 | 4/2009 | Ressemann et al. |
| 7,678,099 B2 | 3/2010 | Ressemann et al. |
| 7,785,315 B1 | 8/2010 | Muni et al. |
| 7,842,062 B2 | 11/2010 | Keith et al. |
| 7,879,061 B2 | 2/2011 | Keith et al. |
| 7,918,871 B2 | 4/2011 | Truitt et al. |
| 8,241,266 B2 | 8/2012 | Keith et al. |
| 8,277,478 B2 | 10/2012 | Drontle et al. |
| 8,282,667 B2 | 10/2012 | Drontle et al. |
| 8,348,969 B2 | 1/2013 | Keith et al. |
| 8,568,439 B2 | 10/2013 | Keith et al. |
| 8,585,728 B2 | 11/2013 | Keith et al. |
| 8,585,729 B2 | 11/2013 | Keith et al. |
| 8,623,043 B1 | 1/2014 | Keith et al. |
| 8,657,846 B2 | 2/2014 | Keith et al. |
| 8,801,670 B2 | 8/2014 | Drontle et al. |
| 8,834,513 B2 | 9/2014 | Hanson et al. |
| 8,882,795 B2 | 11/2014 | Drontle et al. |
| 8,888,686 B2 | 11/2014 | Drontle et al. |
| 8,915,938 B2 | 12/2014 | Keith et al. |
| 8,986,340 B2 | 3/2015 | Drontle et al. |
| 9,005,284 B2 | 4/2015 | Ressemann |
| 9,011,412 B2 | 4/2015 | Albritton, IV et al. |
| 9,101,739 B2 | 8/2015 | Lesch, Jr. et al. |
| 2002/0065455 A1 | 5/2002 | Ben-Haim et al. |
| 2002/0138121 A1 | 9/2002 | Fox |
| 2004/0064083 A1 | 4/2004 | Becker |
| 2004/0064150 A1 | 4/2004 | Becker |
| 2004/0068299 A1 | 4/2004 | Laske et al. |
| 2005/0059931 A1 | 3/2005 | Garrison et al. |
| 2005/0240147 A1 | 10/2005 | Makower et al. |
| 2005/0245906 A1 | 11/2005 | Makower et al. |
| 2006/0004286 A1 | 1/2006 | Chang et al. |
| 2006/0004323 A1 | 1/2006 | Chang et al. |
| 2006/0063973 A1 | 3/2006 | Makower et al. |
| 2006/0095066 A1 | 5/2006 | Chang et al. |
| 2006/0100687 A1 | 5/2006 | Fahey et al. |
| 2006/0106361 A1 | 5/2006 | Muni et al. |
| 2006/0111691 A1 | 5/2006 | Bolmsjo et al. |
| 2006/0149310 A1 | 7/2006 | Becker |
| 2006/0210605 A1 | 9/2006 | Chang et al. |
| 2006/0284428 A1 | 12/2006 | Beadle et al. |
| 2006/0293612 A1 | 12/2006 | Jenson et al. |
| 2007/0005094 A1 | 1/2007 | Eaton et al. |
| 2007/0073269 A1 | 3/2007 | Becker |
| 2007/0129751 A1 | 6/2007 | Muni et al. |
| 2007/0135789 A1 | 6/2007 | Chang et al. |
| 2007/0135803 A1 | 6/2007 | Belson |
| 2007/0167682 A1 | 7/2007 | Goldfarb et al. |
| 2007/0208252 A1 | 9/2007 | Makower |
| 2007/0208301 A1 | 9/2007 | Evard et al. |
| 2007/0249896 A1 | 10/2007 | Goldfarb et al. |
| 2007/0250105 A1 | 10/2007 | Ressemann et al. |
| 2007/0270644 A1 | 11/2007 | Goldfarb et al. |
| 2007/0282305 A1 | 12/2007 | Goldfarb et al. |
| 2007/0293726 A1 | 12/2007 | Goldfarb et al. |
| 2007/0293727 A1 | 12/2007 | Goldfarb et al. |
| 2008/0015472 A1 | 1/2008 | Ressemann et al. |
| 2008/0015540 A1 | 1/2008 | Muni et al. |
| 2008/0082045 A1 | 4/2008 | Goldfarb et al. |
| 2008/0097154 A1 | 4/2008 | Makower et al. |
| 2008/0097239 A1 | 4/2008 | Chang et al. |
| 2008/0097295 A1 | 4/2008 | Makower et al. |
| 2008/0097400 A1 | 4/2008 | Chang et al. |
| 2008/0097514 A1 | 4/2008 | Chang et al. |
| 2008/0097515 A1 | 4/2008 | Chang et al. |
| 2008/0097516 A1 | 4/2008 | Chang et al. |
| 2008/0103521 A1 | 5/2008 | Makower et al. |
| 2008/0119693 A1 | 5/2008 | Makower et al. |
| 2008/0125626 A1 | 5/2008 | Chang et al. |
| 2008/0132938 A1 | 6/2008 | Chang et al. |
| 2008/0154237 A1 | 6/2008 | Chang et al. |
| 2008/0154250 A1 | 6/2008 | Makower et al. |
| 2008/0172033 A1 | 7/2008 | Keith et al. |
| 2008/0195041 A1 | 8/2008 | Goldfarb et al. |
| 2008/0228085 A1 | 9/2008 | Jenkins et al. |
| 2008/0234720 A1 | 9/2008 | Chang et al. |
| 2008/0249500 A1 | 10/2008 | Keith et al. |
| 2008/0269596 A1 | 10/2008 | Revie et al. |
| 2008/0275483 A1 | 11/2008 | Makower et al. |
| 2008/0281156 A1 | 11/2008 | Makower et al. |
| 2008/0287908 A1 | 11/2008 | Muni et al. |
| 2008/0319424 A1 | 12/2008 | Muni et al. |
| 2009/0005763 A1 | 1/2009 | Makower et al. |
| 2009/0028923 A1 | 1/2009 | Muni et al. |
| 2009/0030274 A1 | 1/2009 | Goldfarb et al. |
| 2009/0093823 A1 | 4/2009 | Chang et al. |
| 2009/0187098 A1 | 7/2009 | Makower et al. |
| 2009/0198216 A1 | 8/2009 | Muni et al. |
| 2009/0216196 A1 | 8/2009 | Drontle et al. |
| 2010/0030113 A1* | 2/2010 | Morriss ................ A61B 1/233 600/585 |
| 2010/0168511 A1 | 7/2010 | Muni et al. |
| 2010/0191326 A1* | 7/2010 | Alkhatib ................ A61F 2/013 623/2.11 |
| 2010/0211007 A1 | 8/2010 | Lesch, Jr. et al. |
| 2010/0241155 A1 | 9/2010 | Chang et al. |
| 2010/0274222 A1 | 10/2010 | Setliff, III et al. |
| 2010/0312101 A1* | 12/2010 | Drontle ................ A61B 17/24 600/424 |
| 2011/0071349 A1 | 3/2011 | Drontle et al. |
| 2011/0224652 A1 | 9/2011 | Drontle et al. |
| 2012/0010646 A1 | 1/2012 | Keith et al. |
| 2012/0071727 A1 | 3/2012 | Hanson et al. |
| 2012/0283625 A1 | 11/2012 | Keith et al. |
| 2013/0030458 A1 | 1/2013 | Drontle et al. |
| 2013/0030459 A1 | 1/2013 | Drontle et al. |
| 2013/0041463 A1 | 2/2013 | Ressemann |

(56) References Cited

U.S. PATENT DOCUMENTS

| | | | |
|---|---|---|---|
| 2013/0072958 | A1 | 3/2013 | Ressemann et al. |
| 2014/0350520 | A1 | 11/2014 | Drontle et al. |
| 2014/0357959 | A1 | 12/2014 | Hanson et al. |
| 2014/0364700 | A1 | 12/2014 | Hanson et al. |
| 2014/0378776 | A1 | 12/2014 | Hanson et al. |
| 2015/0031950 | A1 | 1/2015 | Drontle et al. |
| 2015/0045827 | A1 | 2/2015 | Drontle et al. |
| 2015/0105818 | A1 | 4/2015 | Keith et al. |

FOREIGN PATENT DOCUMENTS

| | | | |
|---|---|---|---|
| WO | WO 91/177787 | A1 | 11/1991 |
| WO | WO 96/00033 | A1 | 1/1996 |
| WO | WO 2005/086945 | A2 | 9/2005 |
| WO | WO2010/014799 | A1 | 2/2010 |
| WO | WO 2011/140535 | A1 | 11/2011 |

OTHER PUBLICATIONS

Petersen, Robert J., Canine Fossa Puncture, The Laryngoscope Office, Oct. 5, 1972, pp. 369-371.
Elidan, J., MD., Irrigation of the Maxillary Sinus by Canine Fossa Puncture Experience with 202 Patients, Ann Otol Rhinol Laryngol, 92:1983, pp. 528-529.
Yanagisawa, Eiji, et al., Trans-Canine-Fossa Maxillary Sinoscopy for Biopsy Via the Stammberger Technique, ENT Rhinoscopic Clinic, Aug. 2001 Rhino, pp. 1-3.
Yanagisawa, Eiji, et al., Powered Endoscopic Inferior Meatal Antrostomy Under Canine Fossa Telescopic Guidance, ENT—Ear, Nose & Throat Journal, Sep. 2001, pp. 618-620.
Sathananthar, Shanmugam, et al., Canine Fossa Puncture and Clearance of the Maxillary Sinus for the Severely Diseased Maxillary Sinus, The Laryngoscope 115: Jun. 2005, pp. 1026-1029.
Robinson, Simon, et al., Patterns of Innervation of the Anterior Maxilla: A Cadaver Study with Relevance to Canine Fossa Puncture of the Maxillary Sinus, Laryngoscope 115: Oct. 2005, pp. 1785-1788.
Bolger, William, E., et al., Catheter-Based Dilation of the Sinus Ostia: Initial Safety and Feasibility Analysis in a Cadaver Model, Maryland Sinus Clinic, Bethesda, Maryland, and California Sinus Institute, Palo Alto, California, OceanSide Publications, Inc., May-Jun. 2006, vol. 20, No. 3, pp. 290-294.
Friedman, Michael, M.D. et al., Functional Endoscopic Dilatation of the Sinuses (FEDS): Patient Selection and Surgical Technique, Operative Technologies in Otolaryngology, vol. 17, No. 2, Jun. 2006, pp. 126-134.
Jones, Nick, Commentary on "Safety and Feasibility of Balloon Catheter Dilation of Paranasal Sinus Ostia: A Preliminary Investigation", Annals of Otology, Rhinology & Laryngology 115(4), pp. 300-301 (2006).
Bolger, William E., Commentary Misconceptions Regarding Balloon Catheter Dilation of Paranasal Sinus Ostia, Annals of Otology, Rhinology & Laryngology 115(10): 791-792 (2006).
Lanza, Donald, C., et al., Commentary Balloon Sinuplasty: Not Ready for Prime Time, Annals of Otology, Rhinology & Laryngology 115(10): 789-790 (2006).
Brown, Christopher, L., et al., "Safety and Feasibility of Balloon Catheter Dilation of Paranasal Sinus Ostia: A Preliminary Investigation", Annals of Otology, Rhinology & Laryngology 115(4):293-299 (2006).
Gottman, D., et al., "Balloon Dilatation of Recurrent Ostia Occlusion of the Frontal Sinus", ECR Mar. 3, 2001, 2:-3:30 PM, Vienna Austria (1 page).
Entellus Medical, 510(k) Premarket Notification cover letter and Attachment B: Predicate Device Labeling, dated Aug. 15, 2007.
R. Peterson, Sinus Puncture Therreapy: Canine Fossa Puncture Method "How I Do It" Head and Neck, The Larynsgoscope 91: Dec. 1981, pp. 2126-2128.
T.G.A. Ijaduola, Use of a Foley Catheter for Short-Tem Drainage of Frontal Sinus Surgery, Journ. of Laryngology and Otology, Apr. 1989, vol. 103, pp. 375-378.
A. Gatot et al., Early Treatment of Oribital Floor Fractures with Catheter Balloon in Childre, Int'l J. of Ped. Otorhinolaryngology, 21 (1991) 97-101.
D.I. Tarasov et al., Treatment of Chronic Ethmoiditis by IntraCellular Administration of Medicines to the Ethmoidal Labyrinth, Vestn Otorinolaringol. Nov.-Dec. 1978; (6):45-47 (Abstract in English).
J.M. Robison, Pressure Treatment of Maxillary Sinusitis, J.A.M.A., May 31, 1952, pp. 436-440.
J.M. Robison, Pressure Treatment of Purulent Maxillary Sinusitis, Texas State Journal of Medicine, May 1952, pp. 281-288.
Entellus Medical, 510(k) Letter (Amendment 1) and Attachment D&E, dated Mar. 13, 2008.
Gottman et al., Balloon Dilation of Recurrent Ostial Occlusion of the Frontal Sinus, Gottman et al.: Abstract (B-0453) Mar. 2001, 22 pages.
PCT International Search Report for PCT/US2007/088834, Applicant: Entellus Medical, Inc., Forms PCT/ISA/220 and PCT/ISA/210, dated May 20, 2008 (4 pages).
PCT Written Opinion for PCT/US2007/088834, Applicant: Entellus Medical, Inc., Forms PCT/ISA/237, dated May 20, 2008 (10 pages).
PCT International Search Report for PCT/US2007/66187, Applicant: Entellus Medical, Inc., Forms PCT/ISA/220 and PCT/ISA/210, dated Apr. 17, 2008 (5 pages).
PCT Written Opinion for PCT/US2007/66187, Applicant: Entellus Medical, Inc., Forms PCT/ISA/237, dated Apr. 17, 2008 (5 pages).
Folweiler, David S., Nasal Specific Technique as Part of a Chropractic Approach to Chronic Sinusitis and Sinus Headaches, Journal of Manipulative and Physiological Therapeutics, vol. 18, No. 1 (Jan. 1995).
PCT International Preliminary Report on Patentability (Chapter I of the Patent Cooperation Treaty) of the International Bureau for PCT/US2007/066187, Applicant: Entellus Medical, Inc., Form PCT/IB/326, dated Oct. 30, 2006 (4 pages).
Medtronic, ENT Image-Guided Surgery System, http://www.xomed.com/xomed_products_element.html, Jun. 3, 2009 (2 pages).
International Search Report dated Aug. 2, 2010, for PCT/US2010/037508, Applicant: Entellus Medical, Inc. (4 pages).
Written Opinion of the International Search Authority dated Aug. 2, 2010, for PCT/US2010/037508, Applicant: Entellus Medical, Inc. (4 pages).
International Preliminary Report on Patentability dated Jul. 30, 2009, for PCT/US2007/088834, Applicant: Entellus Medical, Inc. (9 pages).
PCT International Preliminary Report on Patentability (Chapter I of the Patent Cooperation Treaty) for PCT/US2010/037508, Applicant: Entellus Medical Inc., Form PCT/IB/326 and 373, dated Dec. 15, 2011 (6pages).

* cited by examiner

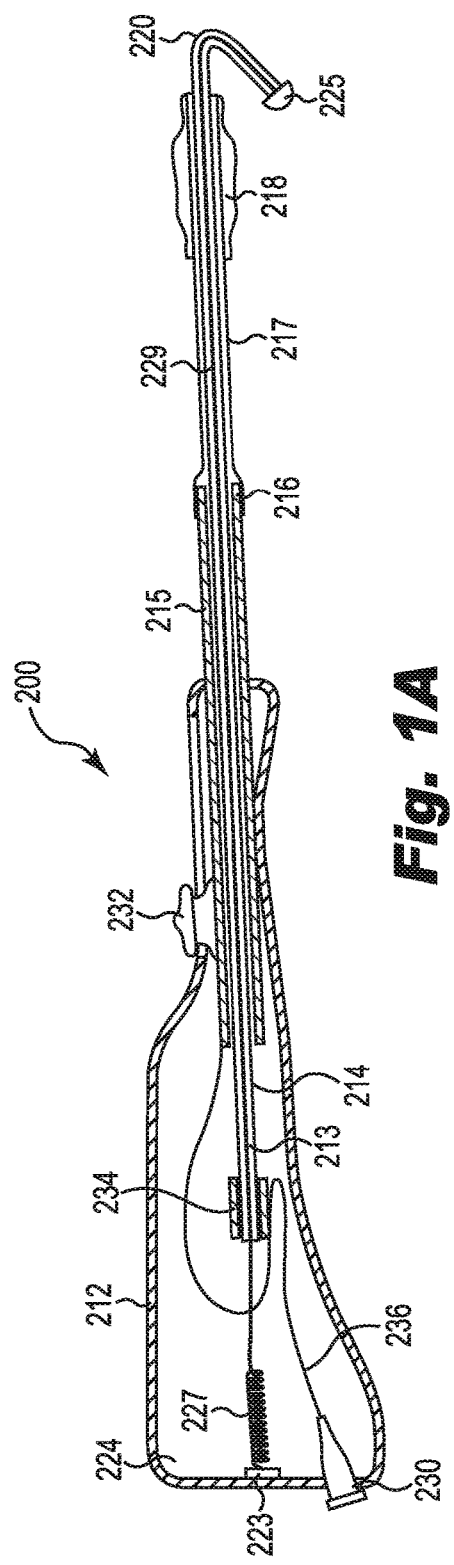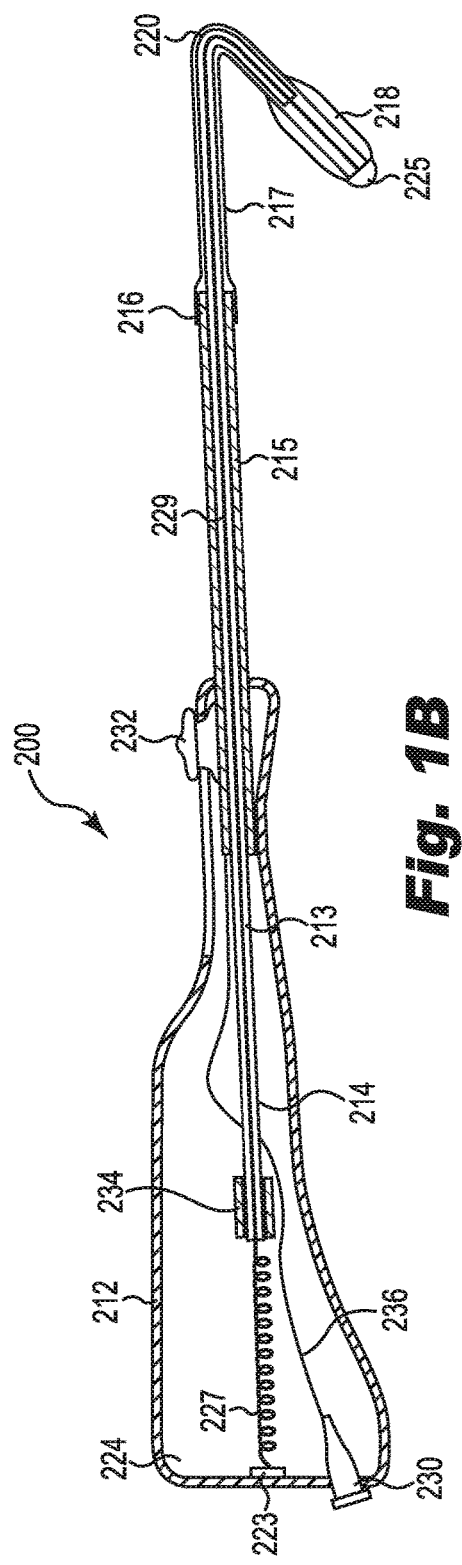

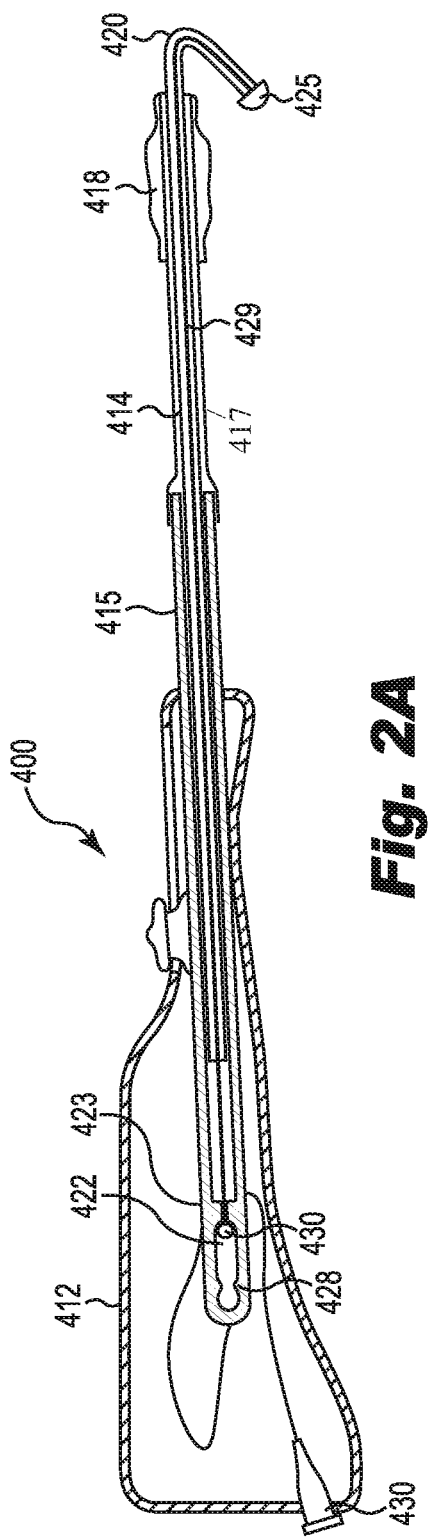
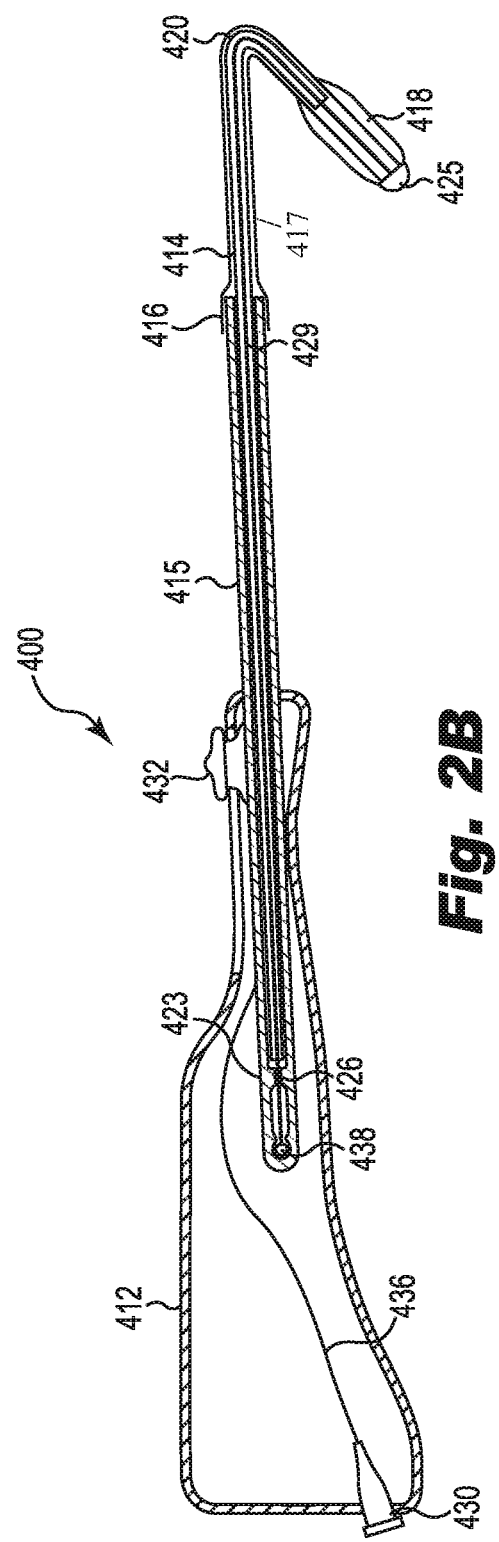

METHODS AND DEVICES FOR TREATING SINUSITIS

RELATED APPLICATION

This Application is a continuation of U.S. application Ser. No. 13/674,734 filed on Nov. 12, 2012, now issued as U.S. Pat. No. 9,283,360, which itself claims priority to U.S. Provisional Patent Application No. 61/558,142 filed on Nov. 10, 2011 and entitled "Methods and Devices for Treating Sinusitis. Priority is claimed pursuant to 35 U.S.C. §§ 119 and 120. The above-noted Patent Applications are incorporated by reference as if set forth fully herein.

BACKGROUND

Sinusitis is a condition affecting over 35 million Americans, and similarly large populations in the rest of the developed world. Sinusitis occurs when one or more of the four paired sinus cavities (i.e., maxillary, ethmoid, frontal, sphenoid) becomes obstructed, or otherwise has compromised drainage. Normally the sinus cavities, each of which are lined by mucosa, produce mucous which is then moved by beating cilia from the sinus cavity out to the nasal cavity and down the throat. The combined sinuses produce approximately one liter of mucous daily, so the effective transport of this mucous is important to sinus health.

Each sinus cavity has a drainage pathway or outflow tract opening into the nasal passage. This drainage passageway can include an ostium, as well as a "transition space" in the region of the ostia, such as the "frontal recess," in the case of the frontal sinus, or an "ethmoidal infundibulum," in the case of the maxillary sinus. When the mucosa of one or more of the ostia or regions near the ostia become inflamed, the egress of mucous is interrupted, setting the stage for an infection and/or inflammation of the sinus cavity, i.e., sinusitis. Though many instances of sinusitis may be treatable with appropriate medicates, in some cases sinusitis persists for months or more, a condition called chronic sinusitis, and may not respond to medical therapy. Some patients are also prone to multiple episodes of sinusitis in a given period of time, a condition called recurrent sinusitis.

Balloon dilation has been applied to treat constricted sinus passageways for the treatment of sinusitis. These balloon dilation devices typically involve the use of an inflatable balloon located at the distal end of a catheter such as a balloon catheter. Generally, the inflatable balloon is inserted into the constricted sinus passageway in a deflated state. The balloon is then expanded to open or reduce the degree of constriction in the sinus passageway being treated to facilitate better sinus drainage and ventilation. At the same time most, if not all, of the functional mucosal tissue lining of the sinuses and their drainage passageways are preserved.

Exemplary devices and methods particularly suited for the dilation of anatomic structures associated with the maxillary and anterior ethmoid sinuses are disclosed, for example, in U.S. Pat. No. 7,520,876 and U.S. Patent Application Publication No. 2008/0172033. Other systems have been described for the treatment of various other sinuses including the frontal sinus. For example, U.S. Patent Application Publication No. 2008/0097295 discloses a frontal sinus guide catheter (FIG. 6B) and method of treating the frontal sinuses (e.g., FIGS. 8B-8C). U.S. Patent Application Publication No. 2008-0125626 discloses another guide device (e.g., FIGS. 10C and 10C') for transnasal access to the frontal sinuses for treatment.

SUMMARY

The invention describes a sinus balloon catheter and methods of use. Specifically the present invention provides a sinus balloon catheter for dilating a sinus cavity lumen. The catheter comprises a guide tube with a proximal and distal end, a sleeve member, a balloon disposed upon the sleeve member and an extendable rounded tip coupled to the distal end.

BRIEF DESCRIPTION OF THE DRAWINGS

The invention is best understood from the following detailed description when read in connection with accompanying drawings, in which:

FIGS. 1A and 1B illustrate cross-sectional side views of a balloon dilation catheter according to one embodiment.

FIGS. 2A and 2B illustrate cross-sectional side views of a balloon dilation catheter according to one embodiment.

DETAILED DESCRIPTION OF THE ILLUSTRATED EMBODIMENTS

Figure 3A:
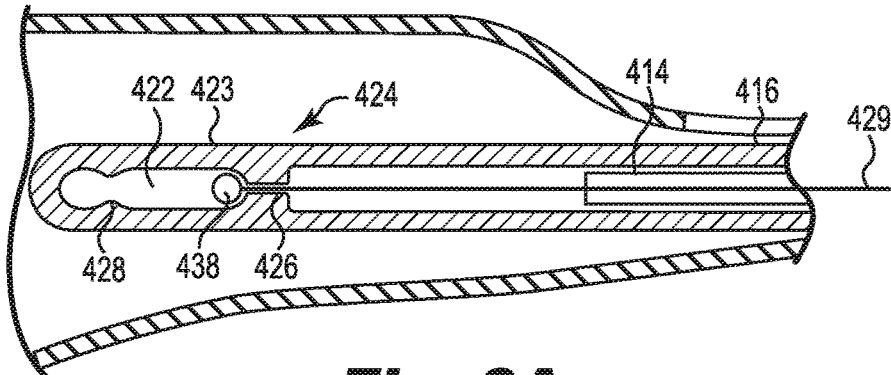
FIGS. 3A-3D illustrate a sequential series of cross-section side views of a portion of a balloon dilation catheter according to one embodiment.

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, and logical changes may be made without departing from the scope of the present invention. The following detailed description is, therefore, not to be taken in a limiting sense, and the scope of the present invention is defined by the appended claims and their equivalents.

In this document, the terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

U.S. Patent Application Publication No. 2010/0312101, the entire teachings of which are incorporated herein by reference, was filed by Drontle, et al. on Jun. 5, 2009. Drontle, et al. describe sinus balloon dilation catheters that includes a balloon and shaft slidably mounted on a substantially rigid inner guide member. To treat a sinus cavity of a subject, the substantially rigid inner guide member is advanced into a drainage pathway of the sinus cavity via a nasal passageway. The shaft and balloon are advanced in a distal direction over the substantially-rigid inner guide member to place the balloon in the drainage pathway. The balloon is inflated to expand or otherwise remodel the drainage pathway.

PCT publication No. WO 2011/140535, the entire teachings of which are incorporated herein by reference, was filed by Ressemann, et al. on May 7, 2011. Ressemann, et al. describe sinus balloon dilation catheters that include a guide tube, a sleeve member annularly positioned over the guide tube, and a balloon coupled to the sleeve member. The sleeve member and balloon can be advanced over the guide tube to a position at or beyond the end of the guide tube. To treat a sinus cavity of a subject, the guide tube is advanced to a position within or near a sinus drainage pathway of the sinus cavity via a nasal passageway. The sleeve member and balloon are advanced over the guide tube to a position at or beyond the distal end of the guide tube. The balloon is inflated to expand or otherwise remodel the drainage pathway.

It has been discovered that when a tubular guide or substantially rigid inner guide member is pre-shaped into a bend and a sleeve member or balloon shaft is situated over that bend for an extended period of storage time (e.g., weeks, months or years), the bend of the guide may impart a bend or deformity into the material of the distal portion of the sleeve member. Such an imparted bend in the sleeve member material may cause the sleeve member to move into undesired positions if translated off of a distal end of the tubular guide. Applicants have recognized this long-term storage problem and some of the embodiments of the present invention are directed towards solutions to that problem. It will be apparent to those of skill in the art that the features found in the balloon catheters described by Drontle, et al. and Ressemann, et al. can be incorporated into the various embodiments of the present invention.

FIGS. 1A and 1B illustrate one embodiment of the present invention in the form of balloon dilation catheter 200. Balloon dilation catheter 200 includes handle 212, substantially rigid inner guide member 214, and sleeve member 216. Handle 212 is configured to be gripped or otherwise manipulated by an operator. Sleeve member 216 is configured to slide longitudinally over inner guide member 214 and off the distal end of inner guide member 214.

Inner guide member 214 defines lumen 213 and is statically secured to handle 212 at guide member attachment point 234. The distal end of inner guide member 214 is made of a malleable material (e.g., a stainless steel hypotube) and allows an operator to bend the distal tip of inner guide member 214 to any desired angle relative to more proximal portions of inner guide member 214. As shown in FIGS. 1A and 1B, distal end has been shaped to include bend 220 so that the distal portion of inner guide member 214 forms an angle of approximately 120 degrees relative to more proximal portions of guide member 214. As used herein, the term "malleable" refers to a material or element of the invention that is capable of being shaped, bent, or otherwise deformed by forces typically produced by manual manipulation of a human user so that the material or element retains the deformation. In this manner, a user of catheter 200 can impart a desired angle to guide member 214 and manipulate handle 212 to better negotiate the tortuous anatomy of the nasal and nasal sinus system with guide member 214.

Sleeve member 216 defines a lumen through which extends inner guide member 214. Sleeve member 216 includes proximal rigid portion 215 and distal flexible portion 217. Proximal rigid portion 215 is secured to balloon advancement member 232. A proximal end of distal flexible portion 217 is secured to the distal end of proximal rigid portion 215. Sleeve member 216 includes balloon 218 (which can be either a compliant or non-compliant balloon) which is in fluidic communication with inflation port 230 via inflation lumen 236 in a manner similar to that taught in incorporated U.S. Patent Application Publication No. 2010/0312101. Inflation lumen 236 is sufficiently long to allow for the full distal extension of balloon 218. Flexible portion 217 is made of a soft or compliant material (e.g., polyethylene or PEBAX). As used herein, the terms "soft" and "compliant" refers to materials or elements of the invention that are capable of being shaped, bent, or otherwise deformed by relatively small forces (e.g., those typically produced by manual manipulation of a human user or from slight pressure by being pressed against tissue) but do not retain the deformation once the force is removed. "Soft" and "compliant" materials are not malleable. While FIGS. 1A and 1B illustrate rigid portion 215 and flexible portion 217 as two separate elements that have been secured together, in some embodiments sleeve member 216 is formed form a single portion of material that includes sufficient column strength to be advanced along guide member 214 while also having sufficient flexibility so as to contour to the shape of the distal end of guide member 214.

Catheter 200 also includes rounded tip member 225 which is secured to the distal end of wire 229. Wire 229 extends through lumen 213. Catheter 200 also includes a means for moving rounded tip member 225 in the form of spring 227. Spring 227 is secured to a proximal end of wire 229 and to the handle at spring attachment point 223 at proximal end 224 of catheter 200. In some embodiments, spring 227, wire 229, and/or rounded tip member 225 are formed from a single portion of material while in other embodiments one or more of those elements are formed from separate portions of material that are then secured together.

During use, a physician or other user of catheter 200 imparts the desired shape to the distal end of inner guide member 214 and, while gripping handle 212, inserts end 200 through a patient's nostril. By manipulating handle 212, the user can position the distal end of guide member 214 at a desired location within the nasal or nasal sinus anatomy (e.g., in or near a sinus drainage passage). Once at the desired location, the user advances balloon advancement member 232 distally with a finger of the hand gripping handle 212 to further position balloon 218 at a desired location. This distal advancement of member 232 causes sleeve member 216 to advance distally along inner guide member 214. If member 232 is advanced sufficiently distally, the distal end of sleeve member 216 will contact rounded tip member 225. If member 232 is advanced further and with sufficient force to overcome the tension force supplied by spring 227, the distal end of sleeve member 216 will force rounded tip member 225 away from the distal end of inner guide member 214. When the user has positioned balloon 218 as a desired location within the anatomy, a fluid is directed through inflation port 230 and into balloon 218 to inflate and dilate that portion of the anatomy. After the dilation is complete, the user deflates balloon 218 by evacuating the fluid and slides balloon advancement member 232 proximally to retract sleeve member 216 and balloon 218 back over inner guide member 214.

Spring 227 pulls on wire 229 urging rounded tip member 225 against the distal end of either sleeve member 216 or inner guide member 214 during positioning of the distal end of inner guide member 214 at the desired location within the anatomy and during advancement and retraction of balloon 218. Rounded tip member 225 protects delicate anatomy from being damaged by the distal end of sleeve member 216 or inner guide member 214.

FIG. 1A illustrates catheter 200 in a retracted position, with balloon advancement member 232 at a relatively proximal position relative to most portions of handle 212. FIG. 1B illustrates catheter 200 in an extended position, with balloon advancement member 232 at a position distal relative to most portions of handle 212 and balloon 218 fully inflated.

Another embodiment of the invention is illustrated in FIGS. 2A and 2B in the form of balloon dilation catheter 400.

Balloon dilation catheter 400 includes handle 412 and sleeve member 416. Sleeve member 416 includes proximal rigid portion 415 and distal flexible portion 417. Sleeve member 416 also includes balloon 418 disposed on distal flexible portion 417. Balloon 418 is in fluidic communication with inflation port 430 and inflation lumen 436. Sleeve member 416 defines a lumen through which extends substantially rigid inner guide member 414. At least the distal end of substantially rigid inner guide member 414 is malleable and can be shaped by a user (e.g., into bend 420). Sleeve member 416 is slidably disposed on rigid inner guide member 414. Balloon advancement member 432 is secured to sleeve member 416. Rounded tip member 425 is secured to the distal end of wire 429. Wire 429 is disposed within a lumen defined by inner guide member 414. Inner guide member 414 is secured to handle 412 by one or more static attachment points (not illustrated) that extend through longitudinal windows in sleeve member 416 and hold guide member 414 static relative to handle 412.

Figure 4:
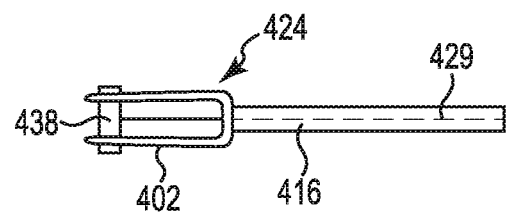
FIG. 4 illustrates a top view of a portion of a balloon dilation catheter according to one embodiment.
Figure 5:
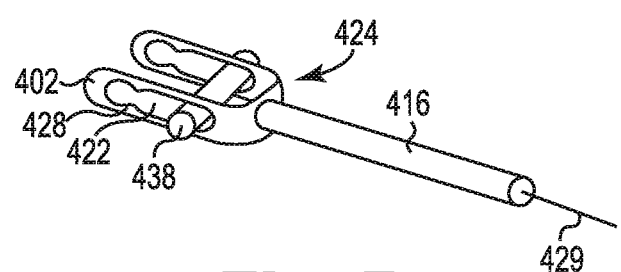
FIG. 5 illustrates a perspective view of a portion of a balloon dilation catheter according to one embodiment.

Many of the components of balloon dilation catheter 400, as well as its use, are similar to those found in balloon dilation catheter 200. However, balloon dilation catheter 400 includes a means for moving rounded tip member 425 that is different from spring 227 of balloon dilation catheter 200. FIGS. 4 and 5 illustrate portions of catheter 400 that form the means for moving rounded tip member 425 of catheter 400.

The means of moving rounded tip member 425 includes end portion 424 and bar 438. End portion 424 forms proximal end 423 of sleeve member 416 (alternatively, end portion 424 is formed from a separate portion of material and is secured to the proximal end of sleeve member 416) and includes a pair of parallel prongs 402. Each prong 402 defines a slot 422 and detents 428. Bar 438 is disposed within slot 422. A proximal portion of wire 429 extends through narrowed wire lumen 426 and between prongs 402. The proximal end of wire 429 is secured to or forms bar 438. Each slot 422 of prongs 402 is partially divided into distal and proximal portion by detents 428.

The ends of bar 438 are also movably secured to handle 412 within a longitudinal sliding track (not illustrated) attached to or formed by the handle. The longitudinal sliding track restrict the movement of bar 438 to generate enough force to cause bar 438 to pass over detents 438. In some alternative embodiments bar 438 is not movably secured to handle 412 and instead detents 428 are shaped to allow bar 438 to pass across detents 438 with less force in one direction (e.g., passing from a distal to a proximal position, relative to detents 438) than in another direction (e.g., passing from a proximal to a distal position, relative to detents 438), so that bar 438 can more easily pass into one portion of slots 422 (e.g., the portion of slots 422 proximal to detents 438) than out of that portion. For example, one side of detents 438 may be formed with a steeper angle relative to the opposite side of detents 438.

FIGS. 3A-3D illustrate a sequential series of cross-section views of the means for moving rounded tip member 425 (for clarity, FIGS. 3A-3D omit some elements of catheter 200) as sleeve member 416 is advanced and retracted.

FIGS. 2A and 3A illustrate catheter 400 when balloon advancement member 432 is in its fully proximal position, with sleeve member 416 retracted onto inner guide member 414. In this position, bar 438 is pressed against the distal end of slots 422, creating a tensioning force in wire 429 and urging rounded tip member 425 against the distal end of inner guide member 414.

Figure 3B:
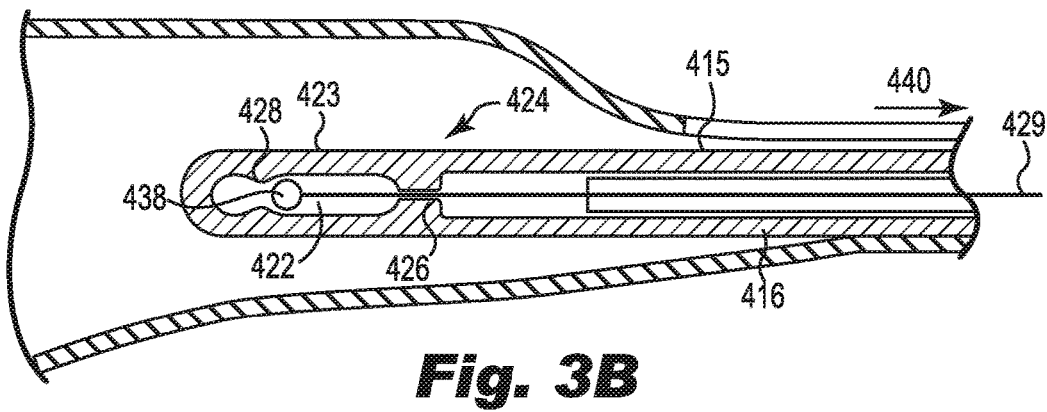

FIG. 3B illustrates catheter 400 after balloon advancement member 432 has been slid parallel to direction 440 to a position distal relative to its positions in FIGS. 2A and 3A. By sliding balloon advancement member 432 distally relative to handle 412, sleeve member 416 is advanced distally along inner guide member 414. Slots 422 also advance distally relative to bar 438 and wire 429 until bar 438 abuts detents 428 at which point further distal advancement of member 432 presses detents 428 against bar 438 and drives wire 429 and rounded tip member 425 distally as well. In some embodiments, the length of the portion of slots 422 that is distal to detents 428 is approximately equal to the length of the distal portion of inner guide member 414 that extends from the distal end of sleeve member 416 when balloon advancement member 432 is in the fully proximal position illustrated in FIG. 2A. This ensures that rounded tip member 425 is positioned adjacent to the distal end of sleeve member 416 when the distal end of sleeve member 416 is advanced past the distal end of inner guide member 414 and ensures that the distal end of sleeve member 416 does not scrape or otherwise damage the delicate tissue of nasal or nasal sinus systems.

Figure 3C:
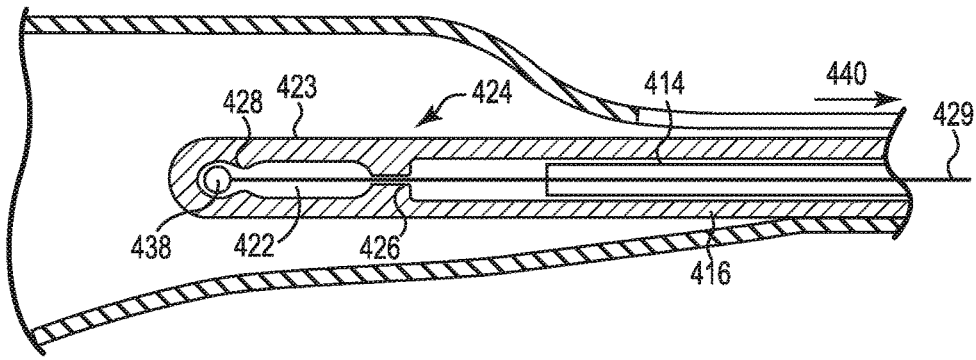

FIGS. 2B and 3C illustrate catheter 400 when balloon advancement member 432 is in its fully distal position, with the distal end of sleeve member 416 fully extended off of the distal end of inner guide member 414. Sliding balloon advancement member 432 to its fully distal position forces bar 438 over detents 428 and into the smaller portion of slots 422 proximal to detents 428.

Figure 3D:
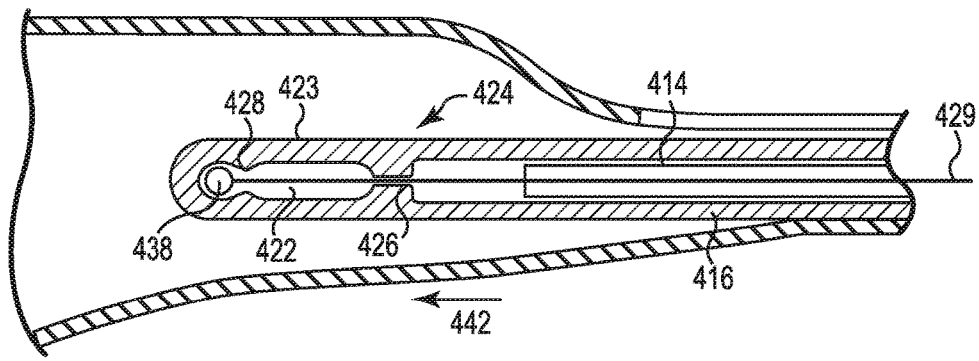

FIG. 3D illustrate catheter 400 when balloon advancement member 432 is slid back along direction 442 to a more proximal position than shown in FIGS. 2B and 3C. Detents 428 hold bar 438 within the smaller portion of slots 422 proximal to detents 428, thereby ensuring that rounded tip member 425 is positioned adjacent to the distal end of sleeve member 416 as balloon advancement member 432 is retracted proximally. When rounded tip member 425 contacts inner guide member 414, inner guide member 414 presses against rounded tip member 425 and produces sufficient tension in wire 429 to force bar 438 distally over detents 428 and back into the larger portion of slots 422 distal to detents 428.

The spring-based means for moving rounded tip member of catheter 200 and the bar-based means for moving rounded tip member of catheter 400 may provide some dissimilar benefits that could be advantageous in different situations. For example, the spring-based embodiment of catheter 200 may be advantageous in sinus treatment procedures where the user desires some form of constant tension pulling the rounded tip member against the distal ends of the inner guide member or sleeve member. In another example, the bar-based embodiment of catheter 400 may be advantageous in sinus treatment procedures where the user does not want to apply a constant counter-force to keep the sleeve member and balloon at a desired extended location.

Figure 6:
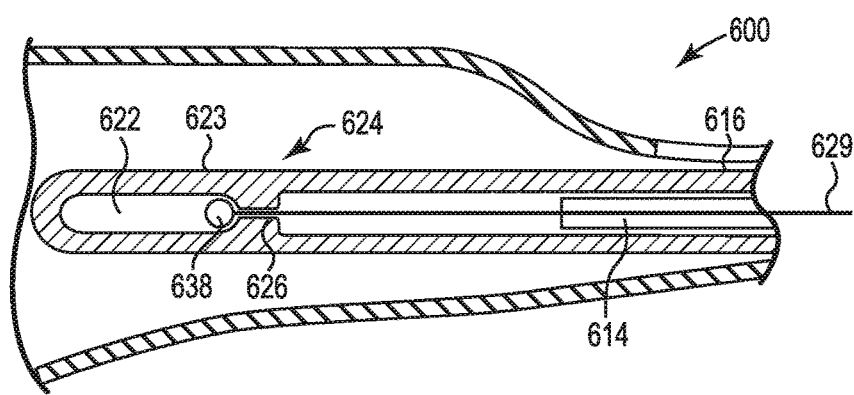
FIG. 6 illustrates a cross-sectional side view of a portion of a balloon dilation catheter according to one embodiment.

FIG. 6 illustrates a portion of another embodiment of the invention in the form of balloon dilation catheter 600. Balloon dilation catheter 600 is the same in most regards as balloon dilation catheter 400, with the exception that catheter 600 has a different means for moving a rounded tip member in the form of ball 638 positioned within chamber 622 of end portion 624. End portion 624 forms proximal end 623 of sleeve member 616, or, alternatively, is formed from a separate portion of material that is attached to the proximal end of sleeve member 616. Ball 638 is secured to or formed by the proximal end of wire 629. Wire 629 extends through wire lumen 626 and a lumen defined by inner guide member 614. When the balloon advancement member of catheter 600 is slid distally to extend sleeve member 616 over and off of the end of the distal tip of inner guide member 614, ball 638 is driven forward by contact with the proximal end of chamber 622, thereby forcing the rounded tip member of catheter 600 forward. When the balloon advancement member of catheter 600 is slid proximally to retract sleeve member 616 back over the inner guide member 614, ball 638 is urged back by the distal side wall of chamber 622. In some embodiments of the invention, chamber 622 includes detents that segment chamber 622 into proximal and distal portions and provide resistance against movement of ball 638 within chamber 622. In still further embodiments, the detents within chamber 622 are shaped in a way that allow ball 638 to pass from a distal to a proximal portion of chamber 622 with less force than is required to pass the ball from the proximal portion to the distal portion of chamber 622.

While embodiments of the present invention have been shown and described, various modifications may be made without departing from the scope of the present invention. Relative sizes and dimensions shown in the various figures can be altered in order to suite a specific application. Accordingly, the invention is defined by the recitations in the claims appended hereto and equivalents thereof.

The invention claimed is:

1. A device for dilating a drainage pathway of a sinus cavity, comprising
    a handle;
    an inner guide member secured to the handle and defining a first lumen;
    a sleeve member defining a second lumen, wherein the inner guide member is at least partially disposed within the second lumen;
    a balloon disposed on the sleeve member;
    a rounded tip member disposed at a position that is distal to a distal tip of both the sleeve member and the inner guide member, the rounded tip member secured to a wire that extends proximally through the first lumen of the inner guide member and terminates in a ball;
    an end portion forming a proximal end of the sleeve member and disposed inside the handle, the end portion including a chamber and having at least one detent therein that segments the chamber into a proximal chamber portion and distal chamber portion, wherein the ball is located in the chamber; and
    a balloon advancement member configured to advance the sleeve member along the inner guide member.

2. The device of claim 1, wherein the at least one detent in the chamber provides resistance against distal advancement of the wire relative to the distal tip of the sleeve member.

3. The device of claim 1, wherein the balloon member is configured to advance off the distal tip of the inner guide member.

4. The device of claim 1, wherein the rounded tip member is configured to move relative to only one of the tip of the sleeve member or the tip of the inner guide member at any one time.

5. The device of claim 4, wherein the end portion and ball are configured to move with the sleeve member.

6. The device of claim 1, wherein the end portion and the ball are configured to advance or retract relative to the inner guide member.

7. A method of treating a sinus cavity of a patient, comprising:
    providing the balloon dilation catheter comprising:
        an inner guide member defining a first lumen;
        a sleeve member defining a second lumen, wherein the inner guide member is at least partially disposed within the second lumen;
        a balloon disposed on the sleeve member;
        a rounded tip member disposed at a position that is distal to a distal tip of both the sleeve member and the inner guide member;
        a balloon advancement member configured to advance the sleeve member along the inner guide member; and;
        a means for moving the rounded tip member;
    directing a distal end of the inner guide member into the head of a patient through a nostril;
    directing the distal end of the inner guide member to a position near a sinus drainage pathway;
    advancing the sleeve member off the distal tip of the inner guide member and to a desired position within the sinus drainage pathway, wherein the rounded tip member remains next to the distal end of the sleeve member during the advancement of the sleeve member; and
    inflating the balloon to dilate the tissue defining the desired position.

8. A method of treating a sinus cavity of a patient, comprising:
    providing the balloon dilation catheter comprising:
        a handle;
        an inner guide member secured to the handle and defining a first lumen;
        a sleeve member defining a second lumen, wherein the inner guide member is at least partially disposed within the second lumen;
        a balloon disposed on the sleeve member;
        a rounded tip member disposed at a position that is distal to a distal tip of both the sleeve member and the inner guide member, the rounded tip member secured to a wire that extends proximally through the first lumen of the inner guide member and terminates in a ball;
        an end portion forming a proximal end of the sleeve member and disposed inside the handle, the end portion including a chamber and having at least one detent therein that segments the chamber into a proximal chamber portion and distal chamber portion, wherein the ball is located in the chamber; and
        a balloon advancement member configured to advance the sleeve member along the inner guide member;
    directing a distal end of the inner guide member into the head of a patient through a nostril;
    directing the distal end of the inner guide member to a position near a sinus drainage pathway;

advancing the sleeve member off the distal tip of the inner guide member and to a desired position within the sinus drainage pathway, wherein the rounded tip member remains next to the distal end of the sleeve member during the advancement of the sleeve member; and
inflating the balloon to dilate the tissue defining the desired position.

\* \* \* \* \*